(12) United States Patent
Silverberg et al.

(10) Patent No.: US 10,849,859 B2
(45) Date of Patent: Dec. 1, 2020

(54) ACRYLIC POLYMERS AND THEIR USE IN TRANSDERMAL DRUG DELIVERY

(71) Applicant: HENKEL IP & HOLDING GMBH, Duesseldorf (DE)

(72) Inventors: Eric N. Silverberg, Summit, NJ (US); Young Taek Choi, Basking Ridge, NJ (US)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 26 days.

(21) Appl. No.: 15/442,820

(22) Filed: Feb. 27, 2017

(65) Prior Publication Data

US 2017/0165205 A1 Jun. 15, 2017

Related U.S. Application Data

(63) Continuation of application No. PCT/US2015/046463, filed on Aug. 24, 2015.

(60) Provisional application No. 62/041,286, filed on Aug. 25, 2014.

(51) Int. Cl.
| | |
|---|---|
| *A61K 9/70* | (2006.01) |
| *A61F 13/02* | (2006.01) |
| *A61K 47/32* | (2006.01) |
| *C08F 220/18* | (2006.01) |
| *C08F 220/14* | (2006.01) |
| *C09J 133/08* | (2006.01) |

(52) U.S. Cl.
CPC ............ *A61K 9/7061* (2013.01); *A61F 13/02* (2013.01); *A61F 13/0253* (2013.01); *A61K 47/32* (2013.01); *C08F 220/14* (2013.01); *C08F 220/18* (2013.01); *C09J 133/08* (2013.01); *A61K 9/7023* (2013.01); *C08F 220/1804* (2020.02); *C08F 2800/20* (2013.01); *C09J 2301/414* (2020.08); *C09J 2433/00* (2013.01)

(58) Field of Classification Search
None
See application file for complete search history.

(56) References Cited

U.S. PATENT DOCUMENTS

| | | | |
|---|---|---|---|
| 3,994,764 | A | 11/1976 | Wolinski |
| 5,561,207 | A | 1/1996 | Wang et al. |
| 2003/0170295 | A1 | 9/2003 | Kim et al. |
| 2005/0100586 | A1 | 5/2005 | Sournac et al. |
| 2008/0181948 | A1 | 7/2008 | Berndl et al. |
| 2015/0045748 | A1* | 2/2015 | Ribeiro Dos Santos ..................... A61K 9/7053 604/290 |

FOREIGN PATENT DOCUMENTS

| | | |
|---|---|---|
| CN | 102090983 A | 6/2011 |
| JP | 2008-266283 A | 11/2008 |
| JP | 2011-74034 A | 4/2011 |
| JP | 2014051467 A | 3/2014 |
| JP | 2014-167036 A | 9/2014 |
| JP | 2015-193542 A | 11/2015 |
| JP | 2015-193543 A | 11/2015 |
| JP | 2015-196647 A | 11/2015 |
| RU | 2351318 C2 | 4/2009 |
| WO | 2007035940 A2 | 3/2007 |
| WO | 2011010556 A1 | 1/2011 |
| WO | 2012097253 A1 | 7/2012 |
| WO | WO-2013127929 A1 * | 9/2013 ........... A61K 9/7053 |

OTHER PUBLICATIONS

Mare, Vibha S. et al. "Acrylate Terpolymer in Fabrication of Medicated Skin Patches" Polymers for Advanced Technologies, 12, 2001, pp. 466-474.

* cited by examiner

*Primary Examiner* — Dennis J Parad
(74) *Attorney, Agent, or Firm* — Sun Hee Lehmann

(57) ABSTRACT

The present disclosure is directed to random, acrylic copolymers that are useful in transdermal applications. Methods of making and using the described co-polymers are also described.

12 Claims, No Drawings

ACRYLIC POLYMERS AND THEIR USE IN TRANSDERMAL DRUG DELIVERY

TECHNICAL FIELD OF THE INVENTION

The disclosure is directed to acrylic polymers that are useful in, for example, transdermal applications.

BACKGROUND OF THE INVENTION

Transdermal delivery is an effective and convenient method for administering a variety of pharmaceuticals. Many transdermal delivery systems incorporate polymeric materials as, for example, adhesives or solubilizing/dispersive agents. Oftentimes, plasticizers are added to those polymers in order to make them suitable for use in a transdermal delivery device. For example, plasticizers can inhibit crystallization of actives and improve the flux of the active through the stratum corneum.

Plasticizers can have negative effects of transdermal patches. For example, plasticizers can lead to migration and may interfere with the solubility of the therapeutic agent being delivered. There are also concerns regarding the safety of some plasticizers. As a result, it is desirable to develop polymers that require less plasticizer, while maintaining acceptable shear and cold flow properties.

SUMMARY OF THE INVENTION

The present disclosure is directed to random co-polymers including a first monomer that is a butyl acrylate monomer, a 2-ethylhexyl acrylate monomer, an octyl acrylate monomer, or an iso-octyl acrylate monomer and at least 18 weight percent, based on the weight of the random co-polymer, of a second monomer that is a methyl methacrylate monomer, a butyl methacrylate monomer, or an isobutyl methacrylate monomer. Processes for preparing the random co-polymers, as well as methods of using the random co-polymers are also described.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION OF THE INVENTION

The following description of the preferred embodiments is merely exemplary in nature and is in no way intended to limit the disclosure, its application, or uses.

The present disclosure is directed to random co-polymers. These random co-polymers are particularly suitable for use in transdermal patch applications.

In preferred embodiments, the random co-polymers of the disclosure consist essentially of a first monomer that is a butyl acrylate monomer, a 2-ethylhexyl monomer, an octyl acrylate monomer, or an iso-octyl acrylate monomer and at least 18 weight percent, based on the weight of the random co-polymer, of a second monomer that is a methyl methacrylate monomer, a butyl methacrylate monomer, or an isobutyl methacrylate monomer. In other embodiments, the random co-polymers of the disclosure consist of a first monomer that is a butyl acrylate monomer, a 2-ethylhexyl monomer, an octyl acrylate monomer, or an iso-octyl acrylate monomer and a second monomer that is a methyl methacrylate monomer, a butyl methacrylate monomer, or an isobutyl methacrylate monomer. Those skilled in the art will appreciate that the random co-polymers can include minor amounts of polymerization initiators and/or antioxidants that are used in preparing or stabilizing the random co-polymers of the disclosure.

The random co-polymers of the disclosure are prepared by a process comprising combining a first monomer that is a butyl acrylate monomer, a 2-ethylhexyl acrylate monomer, an octyl acrylate monomer, or an iso-octyl acrylate monomer and at least 18 weight percent, based on the weight of the random co-polymer, of a second monomer that is a methyl methacrylate monomer, a butyl methacrylate monomer, or an isobutyl methacrylate monomer, in the presence of a polymerization initiator. These processes can be optionally carried out in the presence of a solvent.

In some embodiments of the disclosure, the random co-polymer consists essentially of the first monomer and the second monomer. In other embodiments, the random co-polymers of the disclosure consist of the first monomer and the second monomer.

In preferred embodiments, the random co-polymer comprises between 18 weight percent and 50 weight percent of the second monomer. For example, the random co-polymer comprises about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 weight percent of the second monomer. In particularly preferred embodiments, the random co-polymer comprises 20 weight percent, 22.5 weight percent, or 30 weight percent of the second monomer, based on the weight of the random co-polymer.

In some embodiments of the disclosure, the weight ratio of the first monomer to the second monomer is about 82:18 to about 50:50. A preferred weight ratio of the first monomer to the second monomer is about 82:18, 81:19, 80:20, 79:21, 78:22, 77:23, 76:24, 75:25, 74:26, 73:27, 72:28, 71:29, 70:30, 69:31, 68:32, 67:33, 66:34, 65:35, 64:36, 63:37, 62:38, 61:39, 60:40, 59:41, 58:42, 57:43, 56:44, 55:45, 54:46, 53:47, 52:48, 51:49, or 50:50.

In other embodiments of the disclosure, the random co-polymer consists essentially of about 70 to 80 weight percent of the first monomer and 20 to 30 weight percent of the second monomer, based on the weight of the random co-polymer. In yet other embodiments, the random co-polymer consists of about 70 to 80 weight percent of the first monomer and 20 to 30 weight percent of the second monomer, based on the weight of the random co-polymer.

In preferred embodiments, the first monomer is butyl acrylate. In some embodiments, the first monomer is 2-ethylhexyl acrylate. In other embodiments, the first monomer is octyl acrylate. In still other embodiments, the first monomer is iso-octyl acrylate. The second monomer is preferably methyl methacrylate. In other embodiments, the second monomer is a butyl methacrylate monomer. In yet other embodiments, the second monomer is an isobutyl methacrylate monomer.

Polymerization initiators that are suitable for producing random polymerization are known in the art. Particularly preferred polymerization initiators include 2,2'-azodi(2-methylbutyronitril) (AMBN), dibenzoyl peroxide, lauryol peroxide, and 2,2'-azobisisobutyronitrile (AIBN).

The processes of the disclosure can be carried out "neat," that is, not in the presence of any solvent. In other embodiments, the processes can be carried out in the presence of a solvent. Preferred solvents are organic solvents, for example, ethyl acetate, acetone, hexane, cyclohexane, heptane, toluene, ethanol, and isopropyl alcohol, or a combination thereof.

The random co-polymers of the disclosure have physical and mechanical properties that are suited for, e.g., transdermal patch applications. Co-polymers that are useful in transdermal applications will have a Tg of less than 0° C. Materials useful in transdermal applications will also have a high shear, which is indicative of a low cold flow, which is desirable for transdermal applications. While increasing the amount of methyl methacrylate in a polymer will increase the resulting shear value of the polymer, it also results in an increase in Tg. The random co-polymers of the disclosure include greater than 18 weight percent of methyl methacrylate, yet they can be incorporated into materials having Tg values of less than 0° C., making them suitable for transdermal applications.

For example, the random co-polymers of the disclosure have a Tg of between about −18° C. and −50° C. Those skilled in the art readily understand that Tg can be calculated experimentally according to known techniques. Alternatively, Tg can be calculated theoretically using the Fox equation.

Adhesives prepared from the co-polymers of the disclosure will have a shear value of greater than 10 at 8.8 psi. Preferably, adhesives prepared from the co-polymers of the disclosure will have a shear value of greater than 20, preferably greater than 40, at 4.4 psi "Creep," also referred to as "cold flow," refers to a material's tendency to move slowly or deform under the influence of mechanical stress. Adhesives prepared from the co-polymers of the disclosure will have cold flow properties that are comparable to those observed with block co-polymer-based adhesives.

The random co-polymers of the disclosure can be used to prepare further compositions for use in administering therapeutic agents. Such compositions comprise any of the random co-polymers described herein and a therapeutic agent. These compositions can optionally include at least one ingredient selected from the group consisting of enhancers, plasticizers, tackifying agents, viscosity modifiers, excipients, diluents, emollients, anti-irritants, opacifiers, pigments, antioxidants, and preservatives.

Useful tackifying agents may include any compatible resins or mixtures thereof such as natural and modified rosins including, for example, as gum rosin, wood rosin, tall oil rosin, distilled rosin, hydrogenated rosin, dimerized rosin, and polymerized rosin; glycerol and pentaerythritol esters of natural and modified rosins, including, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, including, for example, styrene/terpene and alpha methyl styrene/terpene; polyterpene resins having a softening point, as determined by ASTM method E28-58T, of from about 80° C. to 150° C.; phenolic modified terpene resins and hydrogenated derivatives thereof including, for example, the resin product resulting from the condensation, in an acidic medium, of a bicyclic terpene and a phenol.

Also useful are resins that are substantially aromatic. Examples of such resins can be prepared from any substantially aromatic monomers having a polymerizable unsaturated group. Typical examples of such aromatic monomers include the styrenic monomers, styrene, alphamethyl styrene, vinyl toluene, methoxy styrene, tertiary butyl styrene, chlorostyrene, etc., indene monomers including indene, and methyl indene.

Various plasticizing agents or diluents may also be present in the compositions of the disclosure. Suitable diluents will preferably be primarily compatible with the soft (B) block of the acrylic block copolymer. Diluents are liquid or semi-solid materials with a Tg, as determined by DSC, below room temperature. These include plasticizing or extending oils and liquid tackifiers. Liquid tackifiers include rosin derivatives such as rosin alcohol, the methyl ester of rosin and the rosin ester formed by esterifying diethylene glycol with rosin.

Other suitable diluents include aliphatic esters such as phthalic acid esters, adipic acid esters, sebacic acid esters and azelaic acid esters, paraffins such as chlorinated paraffin, and polyalkylene glycols such as polyethylene glycol, polypropylene glycol and polytetramethylene glycol as well as their random or block copolymers. Phthalic acid esters such as dibutyl phthalate, di-n-decyl phthalate, bis-2-ethyhexyl phthalate and diisodecyl phthalate, polypropylene glycol and ditridecyl adipate are particularly preferred diluents for use in the practice of the invention.

An antioxidant or stabilizer may also be included in the compositions described herein in amounts of up to about 3% by weight, more typically in amounts of about 0.5%. Among the stabilizers or antioxidants useful herein are the hindered phenols or hindered phenols in combination with a secondary antioxidant such as distearyl thiodipropionate ("DSTDP") or dilauryl thio-dipropionate ("DLTDP"). Representative antioxidants include: 1,3,5-trimethyl 2,4,6-tris (3,5-di-tert-butyl-4-hydroxybenzy) benzene; pentaerythrityltetrakis-3(3,5-di-tert-butyl-4-hydroxyphenyl) propionate; pentaerythritol tetrakis (3-lauryl thiodipropionate); n-octadecyl-3,5-di-tert-butyl-4-hydroxyphenol)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octyl-thio)-1,3,5-triazine; di-n-octadecyl 3,5-di-tert-butyl-4-hydroxy-benzyl-phosphonate; 2-(n-octylthio) ethyl 3,5-di-tert-butyl-4-hydroxy-benzoate; and sorbitol hexa[3-(3,5-di-tert-butyl-4-hydroxyphenyl)-propionate]. Preferred are IRGAFOS 168, a secondary antioxidant available from Ciba and IRGANOX 1010, a hindered phenol primary antioxidant available from Ciba-Geigy. Other antioxidants include ETHANOX 330, a hindered phenol from Albermarle; SANTOVAR, a 2,5 ditert-amyl hydroquinone from Monsanto; and NAUAGARD P a tris (p-nonylphenyl) phosphite from Uniroyal. Preferred antioxidants include butylated hydroxyanisole (BHA) and butylated hydroxytoluene (BHT).

The compositions of the invention, in addition to the therapeutic agent, may advantageously also contain an effective amount of a penetration enhancer. An effective amount of a penetration enhancer means an amount that provides a selected increase in membrane permeability, rate of administration and amount of therapeutic agent.

Other additives conventionally used in adhesives to satisfy different properties and meet specific application requirements also may be added to the compositions of this disclosure. Such additives include, for example, fillers, pigments, flow modifiers, dyestuffs, which may be incorporated in minor or larger amounts into the adhesive formulation, depending on the purpose.

Preferably, the compositions of the disclosure comprise greater than 60 weight percent of the random co-polymer. In other embodiments, the compositions of the disclosure comprise 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 weight percent of the random co-polymer.

In those compositions of the disclosure that include a plasticizer, the plasticizer comprises less than about 20 weight percent of the plasticizer, based on the weight of the composition. In other embodiments, the plasticizer comprises 19, 18, 17, 16, 15, 14, 13, 12, 11, 10, 9, 8, 7, 6, 5, 4, 3, 2, or 1 weight percent of the plasticizer, based on the weight of the composition.

The therapeutic agents used in the compositions of the disclosure can either be dissolved or dispersed in the random co-polymers. Preferred therapeutic agents include any therapeutic agent suitable for transdermal delivery.

The compositions of the disclosure can be in any form known in the art. One particularly preferred form is a transdermal patch device. The transdermal delivery devices of the disclosure can be made in the form of an article such as a tape, a patch, a sheet, a dressing or any other form known to those skilled in the art. The transdermal delivery devices may be produced in any desirable unit form. A circular form is convenient as it contains no corners which might be easily detached from the skin. In addition to having various shapes, the dosage units produced may come in various sizes. Devices of the disclosure can be placed on the skin and allowed to remain for a time sufficient to achieve or maintain the intended therapeutic effect. The time that constitutes a sufficient time can be selected by those skilled in the art with consideration of the flux rate of the device of the invention and of the condition being treated.

Treatment areas where the delivery devices of the disclosure find use, and examples of therapeutic agents which can be incorporated in the devices of the invention, include treatment for incontinence (oxybutinin), central nervous system conditions (methylphenidate), hormone therapy and birth control (estradiol, testosterone, progestin, progesterone, levonorgestrel) cardiovascular (nitroglycerin, clonidine) and cardiotonics (e.g., digitalis, digoxin), pain management or anti-inflammatory (fentanyl, lidocaine, diclofenac, flurbiprofen), cosmetic (benzoyl peroxide, salicylic acid, vitamin C, vitamin E, aromatic oils), antinauseants (scopalamine), smoking cessation (nicotine), antiinflammatory conditions, both steroidal (e.g., hydrocortisone, prednisolone, triamcinolone) and nonsteroidal (e.g., naproxen, piroxicam) treatments, antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin), antiprotazoals (e.g., metronidazole), antifungals (e.g. nystatin), calcium channel blockers (e.g. nifedipine, diltiazem), bronchodilators (e.g., theophylline, pirbuterol, salmeterol, isoproterenol), enzyme inhibitors such as collagenase inhibitors, protease inhibitors, elastase inhibitors, lipoxygenase inhibitors, and angiotensin converting enzyme inhibitors (e.g., captopril, lisinopril), other anti-hypertensives (e.g., propranolol), leukotriene antagonists, anti-ulceratives such as H2 antagonists, antivirals and/or immunomodulators (e.g., 1-isobutyl-1H-imidazo[4,5-c]quinolin-4-amine, 1-(2-hydroxy-2-methyl-propyl)-1H-imidazo[4,5-c]quinoline-4-amine, and acyclovir), local anesthetics (e.g., benzocaine, propofol), antitussives (e.g., codeine, dextromethorphan), antihistamines (e.g., diphenhydramine, chlorpheniramine, terfenadine), narcotic analgesics (e.g., morphine, fentanyl), cardioactive products such as atriopeptides, anticonvulsants (e.g., carbamazine), immunosuppressives (e.g., cyclosporine), psychotherapeutics (e.g., diazepam), sedatives (e.g., phenobarbital), anticoagulants (e.g., heparin), analgesics (e.g., acetaminophen), antimigrane agents (e.g., ergotamine, melatonin, sumatriptan), antiarrhythmic agents (e.g., flecainide), antiemetics (e.g., metaclopromide, ondansetron), anticancer agents (e.g., methotrexate), neurologic agents such as anxiolytic drugs, hemostatics, anti-obesity agents, and the like, as well as pharmaceutically acceptable salts, esters, solvates and clathrates thereof.

Veterinary drugs may also be conveniently applied using the transdermal drug delivery device of the invention, as well as agricultural and horticultural agents. It will be appreciated that transdermal drug delivery in veterinary and horticultural applications enables more exact dosing, and less waste than administration in the food/irrigation water.

Agricultural and horticultural agents can also be delivers using the devices of the disclosure. For example, orchid growth hormone can be delivered using the devices of the disclosure.

It will be appreciated that transdermal drug delivery in veterinary and horticultural applications enables more exact dosing, and less waste than administration in the food/irrigation water.

The following examples are provided to illustrate compositions, processes, and properties described herein. The examples are merely illustrative and are not intended to limit the disclosure to the materials, conditions, or process parameters set forth therein.

EXAMPLES

Example 1: 70:30 Butyl Acrylate:Methyl Methacrylate

An initial charge containing 126.0 g n-butyl acrylate, 54.0 g methyl methacrylate, 120.0 g ethyl acetate (solvent), and 0.12 g 2,2'-azobisisobutyronitrile (AIBN) (polymerization initiator) was prepared and charged to a 2-L 4-neck round bottom flask equipped with stainless steel stirrer, thermometer, condenser, water bath, and addition funnels. The initial charge was heated to reflux while stirring. At 15 minutes from the start of reflux, a monomer mix containing 84.0 g n-butyl acrylate and 12.0 g methy methacrylate, were simultaneously and uniformly added over a period of 1.0 hours. Also at 15 minutes from the start of reflux, 30.0 g ethyl acetate and 1.2 g AIBN were simultaneously and uniformly added over a period of 3 hours. At the end of the addition, the flask contents were held at reflux for 2.0 hours. At the end of the hold period, 30.0 g ethyl acetate and 1.5 g t-amyl peroxypivalate was added over 1 hour. At the end of the addition, the contents were held at reflux for 1 hour. At the end of the hold period, the contents were cooled to room temperature, 60 g of ethyl acetate added and the solution polymer discharged. The final polymer measured 55.46% total solids and a relative viscosity of 2.76 (ethyl acetate, 2.0 wt % solution).

Example 2: 77.5:22.5 Butyl Acrylate:Methyl Methacrylate

An initial charge containing 139.5 g n-butyl acrylate, 40.5 g methyl methacrylate, 120.0 g ethyl acetate (solvent), and 0.12 g 2,2'-azobisisobutyronitrile (AIBN) (polymerization initiator) was prepared and charged to a 2-L 4-neck round bottom flask equipped with stainless steel stirrer, thermometer, condenser, water bath, and addition funnels. The initial charge was heated to reflux while stirring. At 15 minutes from the start of reflux, a monomer mix containing 93.0 g n-butyl acrylate and 27.0 g methyl methacrylate, were simultaneously and uniformly added over a period of 1.0 hours. Also at 15 minutes from the start of reflux, 30.0 g ethyl acetate and 1.2 g AIBN were simultaneously and uniformly added over a period of 3 hours. At the end of the addition, the flask contents were held at reflux for 2.0 hours. At the end of the hold period, 30.0 g ethyl acetate and 1.5 g t-amyl peroxypivalate was added over 1 hour. At the end of the addition, the contents were held at reflux for 1 hour. At the end of the hold period, the contents were cooled to room temperature, 60 g of ethyl acetate added and the solution polymer discharged. The final polymer measured 55.07% total solids and a relative viscosity of 2.75 (ethyl acetate, 2.0 wt % solution).

Example 3: Comparative Example

Polymers of the disclosure were prepared and their properties were compared to other polymers. The results are shown in Table 1.

Peel experiments were performed similarly to Pressure Sensitive Tape Council (PSTC) 101. A strip of tape was applied to a standard test panel with controlled pressure. The tape was peeled from the panel at 180° angle at a specified rate, during which time the force required to effect peel was measured. In these experiments, the tape was a 1"×6" strip with 1 mil (0.001 inch) thick dry adhesive on one, side with a 2 mil polyester (MYLAR) backing.

Shear experiments were performed according to PSTC 107. A strip of tape was applied to a standard test panel with controlled pressure. The panel was mounted vertically. A standard mass was attached to the free end of the tape and the time to failure was determined. Here, the strip of tape was 1 inch×½ inch and the standard mass was 1 kilogram.

The Tg (rheology) was taken as temperature at which the ratio of the loss modulus to the storage modulus (G"/G') is a maximum. The modulus was measured using TA RDA III Rheometer (8 mm plates, controlled strain, temperature sweep test at constant frequency of 10 radians/second).

Polymer A was prepared from a combination of 61.9 wt. % of 2-ethylhexyl acrylate, 32.4 wt. % of methyl acrylate, and 5.7 wt. % of acrylic acid. Polymer A is a random co-polymer with carboxylic acid functionalities.

Polymer B was prepared from a combination of 32.5 wt. % of 2-ethylhexyl acrylate, 32.5 wt. % of butyl acrylate, 15% of methyl methacrylate, and 20 wt. % of t-octyl acrylate. Polymer B is a random co-polymer that is not functionalized with carboxylic acid moieties.

Polymer C was prepared from combining 89.25 g of Kristalex 3100 (100° softening point, available from Eastman) tackifies and 10.75 g of Plasthall DTDA (ditridecyl adipate, available from HallStar) plasticizer with 100 g of a dry block co-polymer prepared from a combination of 77.5 wt. % of butyl acrylate and 22.5 wt. % of methyl methacrylate.

Polymer D is a random co-polymer of the disclosure prepared from a combination of 77.5 wt. % of butyl acrylate and 22.5 wt. % of methyl methacrylate.

Polymer E was prepared by adding 89.25 g of Kristalex 3100 to 100 g of dry Polymer D.

TABLE 1

|  | Tg, ° C. (calculated) | Tg, ° C. (rheology) | Peel, oz/in | Shear, hrs |
| --- | --- | --- | --- | --- |
| Polymer A | −39.1 | −14.3 | 60 | 2.0 (4.4 psi) |
| Polymer B | −21.8 | −5.4 | 50 | 0.5 (4.4 psi) |
| Polymer C | — | 17.8 | <5 | >50 (8.8 psi) |
| Polymer D | −27.3 |  | 46 | 0.4 (4.4 psi), 0.05 (8.8 psi) |
| Polymer E | 5.68 |  | 0.5 | 79 (4.4 psi), 21 (8.8 psi) |

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

What is claimed:

1. A transdermal patch consisting of:
    (A) a random co-polymer prepared by a process of combining
        (i) a first monomer that is a butyl acrylate monomer, a 2-ethylhexyl acrylate monomer, an octyl acrylate monomer, or an iso-octyl acrylate monomer; and
        (ii) at least 18 weight percent, based on the weight of the random co-polymer, of a second monomer that is a methyl methacrylate monomer, a butyl methacrylate, or an isobutyl methacrylate;
    in the presence of a polymerization initiator and optionally, an organic solvent;
    (B) a therapeutic agent; and
    (C) optionally at least one ingredient selected from the group consisting of enhancer, plasticizer, tackifying agent, viscosity modifier, diluent, emollient, anti-irritant, opacifier, pigment, antioxidants, and preservative
    wherein the therapeutic agent is dissolved or dispersed in the random co-polymer.

2. The transdermal patch of claim 1, wherein the random co-polymer is prepared with 20 weight percent, 22.5 weight percent, or 30 weight percent of the second monomer.

3. The transdermal patch of claim 1, wherein the random co-polymer is prepared with a weight ratio of the first monomer to the second monomer of about 82:18 to about 50:50.

4. The transdermal patch of claim 1, wherein the polymerization initiator is 2,2'-azodi(2-methylbutyronitrile) (AMBN), dibenzoyl peroxide, lauryol peroxide, or 2,2'-azobisisobutyronitrile (AIBN).

5. The transdermal patch of claim 1, wherein the organic solvent is ethyl acetate, acetone, hexane, cyclohexane, heptane, toluene, ethanol, or isopropyl alcohol, or a combination thereof.

6. The transdermal patch of claim 1, wherein the antioxidant is butylated hydroxyanisole (BHA) or butylated hydroxytoluene (BHT).

7. The transdermal patch of claim 1, wherein the random co-polymer has a Tg of between about −18° C. and −50° C.

8. The transdermal patch of claim 1, having a shear value of greater than 10 at 8.8 psi.

9. The transdermal patch of claim 1, wherein the random copolymer is present at a level greater than 60 weight percent of the random co-polymer.

10. The transdermal patch of claim 9, wherein the random copolymer is present at a level greater than 80 weight percent.

11. The transdermal patch of claim 1, wherein the plasticizer is present at a level less than 20 weight percent.

12. The transdermal patch of claim 1, wherein the plasticizer is present at a level less than 10 weight percent.

* * * * *